United States Patent [19]

Shinall

[11] Patent Number: 4,919,264

[45] Date of Patent: Apr. 24, 1990

[54] MEDICAL NEEDLE REMOVING AND DISPOSING SYSTEM

[76] Inventor: Kimberly A. Shinall, 4101 Doubles Ct., Apt. 101, Virginia Beach, Va. 23462

[21] Appl. No.: 228,086

[22] Filed: Aug. 4, 1988

[51] Int. Cl.$^5$ .................... B65D 85/24; B65D 81/18
[52] U.S. Cl. .................................. 206/210; 206/366; 220/1 T
[58] Field of Search ............... 206/366, 364, 365, 305, 206/210; 604/197, 198, 192, 110; 220/1 T

[56] References Cited

U.S. PATENT DOCUMENTS

| | | | |
|---|---|---|---|
| 1,045,607 | 11/1912 | Payne | 206/366 |
| 2,557,222 | 6/1951 | Goode | 206/365 |
| 2,557,420 | 6/1951 | Elliott | 206/366 |
| 2,929,510 | 3/1960 | Penn | 206/366 |
| 3,114,455 | 12/1963 | Claisse et al. | 206/366 |
| 3,876,067 | 4/1975 | Schwarz | 206/209 |
| 4,027,669 | 6/1977 | Johnston et al. | 128/218 |
| 4,367,738 | 1/1983 | Legendre et al. | 128/218 |
| 4,466,538 | 8/1984 | Gianni | 206/366 |
| 4,488,643 | 12/1984 | Pepper | 206/366 |
| 4,795,443 | 1/1989 | Permenter et al. | 604/198 |

FOREIGN PATENT DOCUMENTS 0427154 10/1965 Switzerland ............... 206/366

OTHER PUBLICATIONS

Photocopy of Container for Vogue Floral Clay.

Primary Examiner—Jimmy G. Foster
Assistant Examiner—D. Jenny
Attorney, Agent, or Firm—Griffin, Branigan & Butler

[57] ABSTRACT

A medical needle removing and disposing system (10) comprises a box (12) having a plurality of compartments (14) therein, each for removing a needle assembly (58) from injection and/or blood drawing equipment (62) and for disposing of it. A compartment comprises first and second containers (16, 20) for defining first and second chambers (18, 22) with a needle gripper (24) positioned therebetween. The first container has a plastic, non-hardening, tacky, substance (44) therein. Injection and/or blood drawing equipment with a medical needle assembly mounted thereon can be manipulated to extend a shaft (60) of the needle assembly into the second chamber until a mounting tube (56) of the medical needle assembly is located at the needle assembly remover which grips the mounting tube so that the injection and/or blood drawing equipment can be rotated for unscrewing the mounting tube from the injection and/or blood drawing equipment. The medical needle assembly is left in the dispenser with the shaft buried in the tacky substance.

8 Claims, 2 Drawing Sheets

MEDICAL NEEDLE REMOVING AND DISPOSING SYSTEM

BACKGROUND OF THE INVENTION

A problem that has existed in medical clinics, laboratories, hospitals, doctors offices, and the like for some years is that of safely disposing of medical needle assemblies, such as hypodermic needles and VACUTAINER needles. In this respect, most such medical needle assemblies are currently disposable, however, it is not advisable, and in some cases prohibited by regulation, for these items to be disposed of in normal disposal units. The reason for this is that medical needles could inadvertently be touched by medical and/or non-medical personnel or someone trying to retrieve items from a trash can, and thereby penetrate skin, possibly transmitting deadly diseases. It is also possible that such disposal units could be inadvertently tipped-over so that the medical needles therein could be strewn about, again, inadvertently penetrating skin. In the not to distant past, it was thought that adequate protection was provided by returning medical needles to cover sheaths, which are normally on the needles when they are originally sold, before they are discarded. However, a difficulty is encountered in placing these cover sheaths back on the needles once the needles have been used because in that an operator, who must hold a cover sheath in one hand and a needle in the other, can easily make a mistake, missing the sheath with the needle, and sticking himself or herself therewith instead. Thus, it is an object of this invention to provide a medical needle removing and disposing system which does not involve inserting a medical needle into a hand-held cover sheath.

A number of medical needle removing and disposing systems have been suggested comprising boxes having keyhole shaped openings therein. Injection and/or blood drawing equipment, such as syringes, having needle assemblies mounted thereon are each manipulated by one hand to insert the needle assemblies through large portions of the keyhole shaped openings and to slide noses of the injection and/or blood drawing equipment into narrower slots of the keyhole shaped openings so that the needle assemblies are on the inside of the boxes and most of the injection and/or blood drawing equipment is on the outside of the boxes. The injection and/or blood drawing equipment is then pulled away from the boxes and the edges of the slots impinge on upper shoulders of mounting tubes of the needle assemblies so as to force them off of the noses of the injection and/or blood drawing equipment. The needle assemblies fall into the boxes and the injection and/or blood drawing equipment can be disposed of separately, or sterilized for reuse. A difficulty with such systems is that the boxes usually have removable tops, or covers, so that the needles thereof can be retrieved and reused by unauthorized personnel or can be inadvertently strewn about. Even for such systems that do not have openable covers, needles can shake out of the keyhole shaped openings. It is an object of this invention to provide a medical needle removing and disposing system which does not allow removal of needle assemblies therefrom once they have been properly disposed of and, even if the system is opened with force, does not allow the needle assemblies to be used again for injections.

A further difficulty with the box type disposal systems described above is that many needle assemblies are not mounted on injection and/or blood drawing equipment from which they can be slid off noses thereof. In this respect, many syringes have outer and inner mounting cylinders at the noses thereof, the outer mounting cylinders having internal threads thereon, and the inner mounting cylinders having smooth outer surfaces. Needle assemblies therefor have mounting tubes with outer disk-shaped flanges which screw onto the internal threads of the outer mounting cylinders while the inner mounting cylinders are inserted into the mounting tubes of the needle assemblies. For such injection and/or blood drawing equipment, keyhole shaped slots will not be adequate for removing needle assemblies from injection and/or blood drawing equipment with one hand because they do not allow one to unscrew needle assemblies from injection and/or blood drawing equipment. Thus, it is an object of this invention to provide a medical needle removing and disposing system which allows a user to unscrew a needle assembly from injection and/or blood drawing equipment with one hand at the same time he or she disposes of the needle assembly.

Yet another object of this invention is to provide a medical needle removing and disposing system which will remove and dispose of not only hypodermic needle assemblies but which will also remove and dispose of VACUTAINER-type needle assemblies, having needles at opposite ends thereof.

SUMMARY

A medical needle removing and disposing system comprises a first container having an opening at one end with a needle assembly remover mounted at the opening for engaging a medical needle assembly mounted on injection and/or blood drawing equipment. An operator can manipulate the injection and/or blood drawing equipment to move an elongated rigid needle shaft of the needle assembly into the first container, with the needle assembly remover engaging a mounting tube of the needle assembly. The operator can manipulate the injection and/or blood drawing equipment to remove the needle assembly and thereby leave the needle assembly in this position. A feature of the invention is the needle assembly remover which grips a radially directed outer surface of the needle assembly mounting tube to prevent the rotation thereof so that the operator can unscrew the mounting tube from the injection and/or blood drawing equipment. Another feature of the invention is a tacky, plastic, nonhardening substance which is in the first container for holding the rigid shaft of the needle assembly therein and for stopping up a bore of the rigid shaft so that the needle assembly cannot be used again. Yet another feature is a second container which communicates with the first container via a first chamber opening at the needle assembly remover. In this regard, there is a second chamber opening opposite the first chamber opening of a size sufficiently large for receiving the mounting tube of the medical needle assembly as well as injection and/or blood drawing equipment on which the mounting tube is mounted. This second container has the purpose of holding an oppositely directed needle which some needle assemblies have (such as VACUTAINER needle assemblies). One aspect of the invention is a one-way slidable cover for covering the second chamber opening after a needle assembly has been disposed of therein. In one embodiment there are a plurality of second chambers with one slidable cover servicing them all.

BRIEF DESCRIPTION OF THE DRAWINGS

The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

DESCRIPTION OF THE PREFERRED EMBODIMENT

Figure 1:
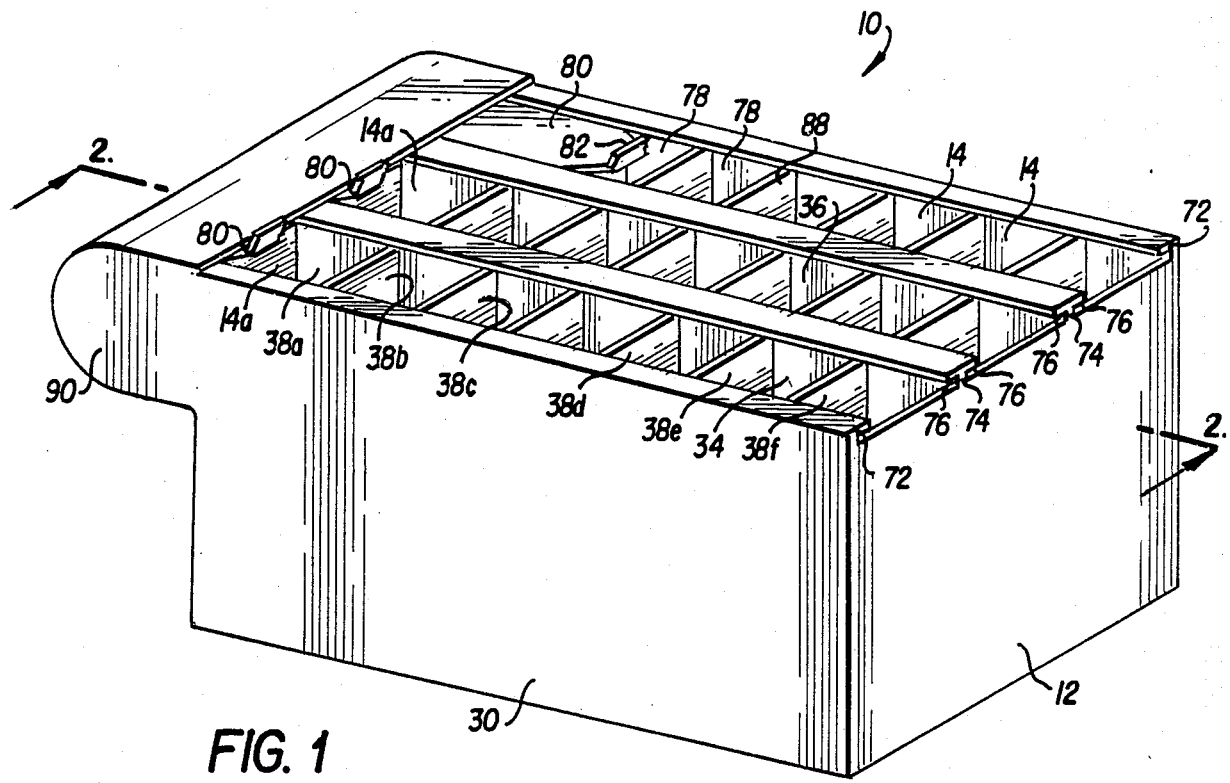
FIG. 1 is an isometric view of a medical needle removing and disposing system of this invention.

A medical needle removing and disposing system 10 comprises a box 12 having a plurality of compartments 14 therein, each for the removal and disposal of one medical needle assembly. Each compartment 14 includes a first container 16 (FIG. 2) defining a first chamber 18, a second container 20 defining a second chamber 22, and a needle assembly remover 24 positioned between the first and second containers 16 and 20. Outside end walls 26 and 28, outside side walls 30 and 32, longitudinal internal walls 34 and 36, cross walls 38a, b, c, etc., round first container walls 40, and a horizontal wall 42 defining the needle assembly removers 24, can all be molded of one piece of plastic, with most of these walls being 1/16 of an inch thick, however, with the horizontal wall 42 being a 1/4 of an inch thick. The first chambers 18 of the first containers 16 need only be slightly larger than the size of a medical needle to be disposed of, and in one preferred embodiment, they are 2 3/4 inches long and approximately 3/16 inches in cross sectional diameter. The second chambers 22 of the second containers 20 need be only slightly larger than the nose of and/or blood drawing equipment which hold the needle assemblies to be disposed of with the medical needle removing and disposing system 10. In a preferred embodiment they are approximately 1/2 inch in height and 1 inch square in cross sectional size.

The first chamber 18 is filled with a nonwater-soluble plastic substance 44 which is nonhardening and which is tacky. The viscosity of this substance should be such that it will not flow under its own weight at normal room temperatures. A finely ground clay or diatamecious earth with a non-drying oil, such as linseed oil, and an antioxidant stabilizer will work in this invention as the substance. A specific example of a substance 44 is a floral clay manufactured and sold by Beagle Manufacturing Co., Inc. of El Monte, California 91731 under the trademark VOGUE, TIP NOT, FLORAL CLAY. This clay is normally used for holding flower arrangements, candles, figurines and the like in place and grips somewhat like glue, although it does not harden. Modeling clay, used by children to model small figures, will also function as the plastic substance 44.

Figure 4:
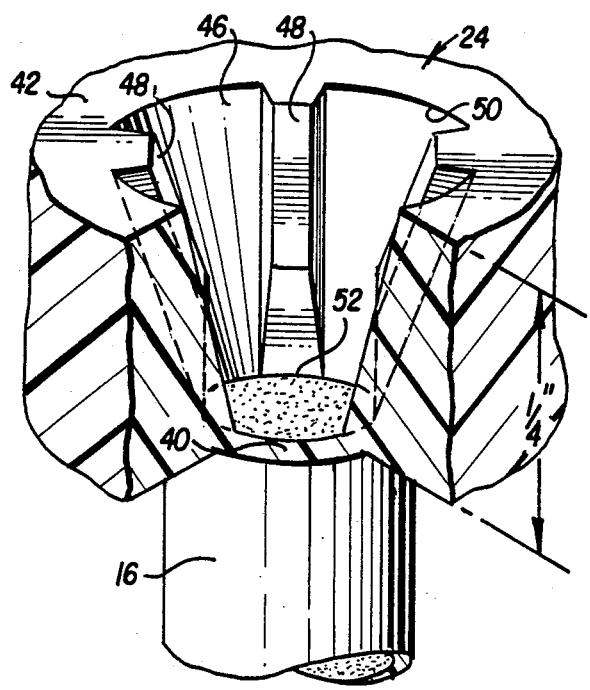
FIG. 4 is an enlarged, isometric, partially cut-away, view of a needle assembly remover of the medical needle removing and disposing system of the other drawings.
Figure 5:
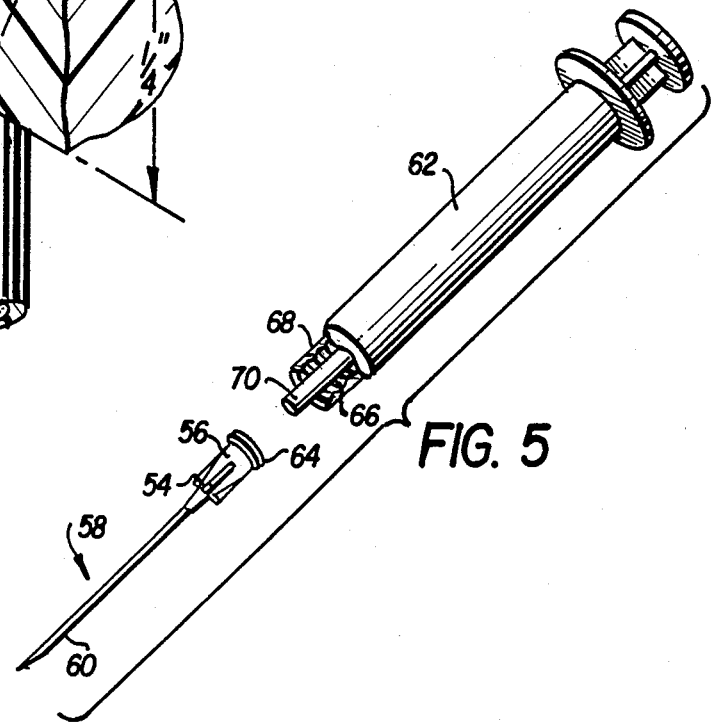
FIG. 5 is a perspective side view of a needle assembly.

The needle assembly remover 24 is shown in more detail in FIG. 4 and is basically a tapered hole 46 with elongated teeth 48 directed radially inwardly from the surface thereof, extending from an entrance opening 50 to an exit opening 52. The entrance opening 50 is approximately 3/8 inch in diameter while the exit opening 52 is approximately 3/16 inches in diameter. Although the teeth 48 are shown protruding rather far in the drawings for illustration purposes, in use, they need protrude only slightly. In this respect, these teeth 48, with the tapered hole 46, form an internal cog which mates with protrusions 54 which are on mounting tubes 56 of needle assemblies 58 (see FIG. 5). By being tapered, the hole 46 and the teeth 48 can accommodate the web protrusions 54 of any reasonably sized needle assembly 58. In this regard, when a rigid shaft, or needle, 60 of a needle assembly 58 is inserted through the needle assembly remover 24 into the first container 16 until the web protrusions 54 of the mounting tube 56 contact the periphery of the tapered hole 46, the web protrusions 54 make contact with the teeth 48 when the injection and/or blood drawing equipment 62, such as a syringe, on which the needle assembly 58 is mounted is rotated. The web protrusions 54 will contact the teeth 48 to prevent the mounting tube 56 from rotating with the injection and/or blood drawing equipment 62 and a disc flange 64 of the needle assembly 58 will be unscrewed from threads 66 of an outer mounting cylinder of the injection and/or blood drawing equipment 62. When this happens, the mounting tube 56 of the needle assembly 58 is dismounted from the outer mounting cylinder 68 and inner mounting cylinder 70.

Figure 2:
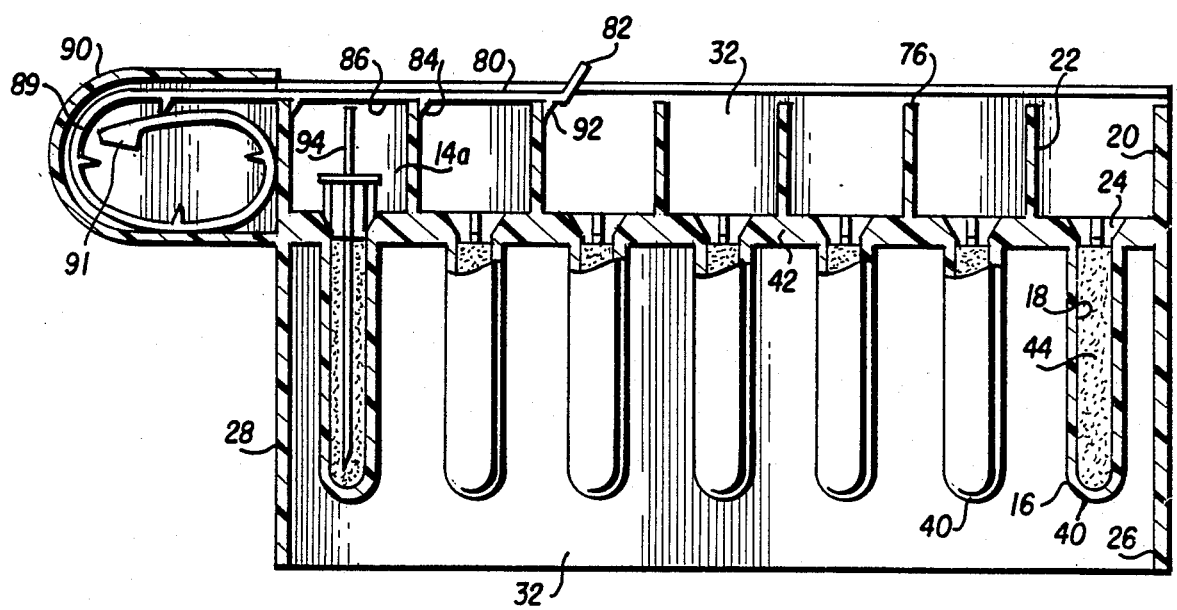
FIG. 2 is a sectional view taken on line 2—2 in FIG. 1.
Figure 3:
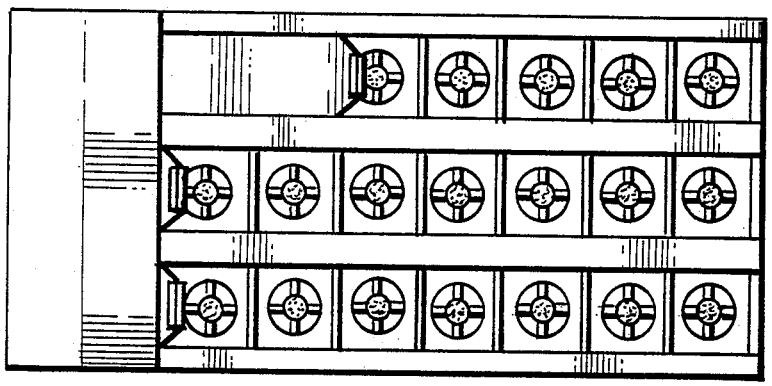
FIG. 3 is a top plan view of the medical needle removing and disposing system of FIG. 1.

Fastened separately on top of the box 12 are side L-shaped tracks 72 and internal T-shaped tracks 74. These tracks form slots 76 on opposite sides of each row of compartments 14, at second chamber openings 78. Elongated, flat, plastic, flexible cover strips 80 respectively ride in these slots 76 with outer ends 82 thereof curling upwardly to be gripped by a user's fingers. Each of these flexible cover strips 80 is at least as long as the box 12 so that it can cover all the second chamber openings 78 in one row of compartments 14. Each flexible cover strip 80 has a width so that it fits snugly in opposite slots 76 but yet can be slid easily therealong. Further, each of the flexible cover strips 80 has rachet teeth 84 on a lower surface 86 thereof which have tapered leading sides to allow them to easily slide over top edges 88 of the cross walls 38a, b, c etc. in the right-hand direction as shown in FIGS. 1 and 2, but which have abrupt following edges which prevent them from sliding back over the top edges 88, in the left-hand, direction as viewed in FIGS. 1 and 2. Before the medical needle removing and disposing system of this invention is used, the handle outer ends 82 of the flexible cover strips 80 are at first compartments 14a such that second chamber openings 78 of the first compartments 14a are uncovered. Remaining portions 90 of the flexible cover strips 80 are rolled up in a covered housing 90 which is attached to the box 12 at the end wall 28 thereof. A first rachet tooth 92 of each flexible cover strip 80 is engaged with the outside end wall 28. Although the flexible cover strips are sufficiently flexible to allow them to be rolled up in the covered housing 90 they are not flexible enough that they could be easily bent along a longitudinal crease to be removed from the slots 76. Enlarged portions 91 prevent the flexible cover strips from being pulled completely through the box 12.

In operation of the medical needle removing and disposing system of the drawings, injection and/or blood drawing equipment 62 (shown as a hypodermic needle in FIG. 5) having a used needle assembly 58 mounted thereon is manipulated so that the rigid shaft, or needle, 60 is inserted through the second chamber opening 78 of one of the first compartments 14a, down through the respective needle assembly remover 24 into the first chamber 18 of the first container 16. The rigid shaft 60 moves into the non-hardening plastic substance 44 in the first chamber 18 until web protrusions 54 on its mounting tube 56 contact the tapered hole 46 of the needle assembly remover 24. Once the operator feels this, he or she rotates the injection and/or blood drawing equipment 62. When this is done, the web protrusions 54 engage the teeth 48 and the needle assembly 58 and the mounting tube 56 is thereby prevented from rotating with the injection and/or blood drawing equipment 62. Thus, the disc flange 64 of the needle assembly 58 is unscrewed from threads 66 on the outer mounting cylinder 68 of the injection and/or blood drawing equipment 62. Once the disc flange 64 is disengaged from the threads 66, the operator lifts the injection and/or blood drawing equipment 62 and discards it elsewhere. The needle assembly 58, however, is held firmly in the tacky plastic substance 44 and stays in that position. The operator then grips the handle outer end 82 of the appropriate flexible cover strip 80 and pulls the cover strip to the right as viewed in FIGS. 1 and 2, a distance of one compartment 14. Since the needle assembly 58 was placed in a compartment 14a, the strip is pulled until the rachet tooth 92 has gone beyond the cross wall 32a.

When the medical needle removing and disposing system 10 is filed, it is incinerated to meet policies of many hospitals.

It will be appreciated by those of ordinary skill in the art that a medical needle assemblY 58 disposed in compartment 14a as described above cannot be removed therefrom because the first rachet tooth 92 will not allow the flexible cover strip 80 to be moved from a position in which it will uncover the compartment 14a. Also it will be appreciated that should the box 12 fall, or be otherwise disturbed, before the flexible cover strip 80 is pulled across the top of the compartment 14a, the needle assembly will not fall out of the box 12 because it is held therein by the tacky plastic substance. Also it will be appreciated that should unauthorized personnel open the box by force, they will not be able to use any of the needle assemblies 58 stored therein because their bores are clogged with the non-hardening tacky plastic substance 44.

The second chambers 20 make it possible to use the medical needle removing and disposing system of this invention for removing and disposing of VACUTAINER-type needle assemblies which have needles at opposite ends thereof as is shown in FIG. 2. In this regard, opposite needles 94 can be positioned in the second containers 20 and they are still below the flexible cover strips 80. After one has inserted a needle assembly into the medical needle removing and disposing system of this invention, there is little danger from that needle due to inadvertence or to unauthorized intent. In this regard, the box would be labeled that the needles can no longer be used, which they cannot be because of the tacky, non-hardening plastic substance.

While the invention has been particularly shown and described with reference to a preferred embodiment, it will be understood by those skilled in the art that various changes in form and detail may be made therein without departing from the spirit and scope of the invention. For example, the box 12 with its various molded parts, could be made of metal rather than plastic, however, it is thought that this would be more expensive. Further, the various walls of the box 12 need not be shaped as depicted and described herein. In this regard, it would be possible to have only one first container 16 filled with clay servicing a plurality of second containers 20. The plastic substance, used for clogging the needles could be a hardening substance, however, if it were, there would be a danger that it would harden too soon or too late. Some provision would have to be made for activating the hardening substance.

The embodiments of the invention in which an exclusive property or privilege are claimed are defined as follows:

1. A medical needle removing and disposing system for removing from injection and/or blood drawing equipment and disposing thereof a medical needle assembly having an elongated rigid shaft affixed on a mounting tube, said removing and disposing system comprising:

a first container defining a first chamber, said first container having a first-chamber opening at one end thereof but being otherwise closed, said first chamber being of a size for receiving said shaft of said medical needle assembly extending therein through said first-chamber opening;

a needle assembly remover means mounted at said first-chamber opening for gripping an outer surface of said mounting tube and thereby preventing said mounting tube from moving and for holding said needle assembly therein to dispose of said needle assembly;

second container defining a second chamber aligned with, and communicating with said first chamber at said first-chamber opening, said second chamber having a second chamber opening opposite said first chamber opening of a size sufficiently large for receiving said mounting tube of said medical needle assembly as well as said injection and/or blood drawing equipment on which said mounting tube is mounted when said injection and/or blood drawing equipment is manipulated to extend said shaft through said second chamber into said first container;

a one-way slidable cover having a racket mechanism thereon to allow said cover to close said second chamber opening, but to prevent said cover from being moved back to a position for uncovering said chamber opening;

whereby, said injection and/or blood drawing equipment with a medical needle assembly mounted thereon can be manipulated to extend said shaft through said first-chamber opening into said first chamber until said mounting tube of said medical needle assembly is located at said needle assembly remover which engages said outer surface of said mounting tube, said injection and/or blood drawing equipment can then be manipulated relative to said needle assembly remover for detaching said mounting tube from said injection and/or blood drawing equipment to leave said medical needle assembly in said medical needle removing and disposing system, and said one-way slidable cover can then be closed.

2. A medical needle removing and disposing system as in claim 1, wherein said needle assembly remover means comprises a tapered hole with radially protruding ridges therein so that said needle assembly remover means can be used with various size needle assemblies.

3. A medical needle removing and disposing system as in claim 1, wherein said second container is sufficiently large to hold an oppositely directed needle when a medical needle assembly is inserted into said first container.

4. A medical needle removing and disposing system as in claim 1, wherein there are a plurality of second containers and needle assembly removers, serviced by one slidable cover.

5. A medical needle removing and disposing system as in claim 1, wherein said first container is filled with a tacky plastic substance for adhering to and clogging the bore of an shaft inserted therein.

6. A medical needle removing and disposing system as in claim 5, wherein there are a plurality of second containers and needle assembly removers, each said second chamber being aligned with, and communicating with, a first chamber at a first chamber opening, each said second chamber having a second chamber opening opposite the respective first chamber opening of a size sufficiently large for receiving said mounting tube of said medical needle assembly as well as said injection and/or blood drawing equipment on which said mounting tube is mounted when said injection and/or blood drawing equipment is manipulated to extend said shaft through said second chamber into said first chamber.

7. A medical needle removing and disposing system as in claim 5, wherein there are a plurality of second containers and needle assembly removers.

8. A medical needle removing and disposing system as in claim 1, wherein there are a plurality of second containers and needle assembly removers, each said second chamber being aligned with, and communicating with, a first chamber at a first chamber opening, each said second chamber having a second chamber opening opposite the respective first chamber opening of a size sufficiently large for receiving said mounting tube of said medical needle assembly as well as said injection and/or blood drawing equipment on which said mounting tube is mounted when said injection and/or blood drawing equipment is manipulated to extend said shaft through said second chamber into said first chamber.

* * * * *